United States Patent [19]

Hon

[11] 4,136,681
[45] Jan. 30, 1979

[54] CATHETER FOR MEASURING INTRAUTERINE PRESSURE

[75] Inventor: Edward H. Hon, Bradbury, Calif.

[73] Assignee: American Home Products Corporation, New York, N.Y.

[21] Appl. No.: 658,821

[22] Filed: Feb. 17, 1976

[51] Int. Cl.² .............................................. A61B 5/00
[52] U.S. Cl. .............................. 128/2 R; 128/2.05 D; 128/349 R
[58] Field of Search .................. 128/2 R, 2 S, 2.05 D, 128/2.05 E, 214.4, 349, 350 V

[56] References Cited

U.S. PATENT DOCUMENTS

| | | | |
|---|---|---|---|
| 3,095,871 | 7/1963 | Mann et al. | 128/2 S |
| 3,559,643 | 2/1971 | Pannier et al. | 128/214.4 |
| 3,570,485 | 3/1971 | Reilly | 128/214.4 |
| 3,720,201 | 3/1973 | Ramsey | 128/2.05 D |
| 3,752,150 | 8/1973 | Harris | 128/2 S |
| 3,835,854 | 9/1974 | Jewett | 128/214.4 |
| 3,958,562 | 5/1976 | Hakim et al. | 128/2 R |

OTHER PUBLICATIONS

Junge, H. D., German Med. Journ.:, "Obstetrics and Gynecology," 29, 2, (Feb. 1969), pp. 129–133.

Primary Examiner—Kyle L. Howell
Attorney, Agent, or Firm—Darby & Darby

[57] ABSTRACT

A catheter is disclosed for measuring the intrauterine pressure of a woman in labor. It comprises an elongated flexible tube which is inserted into the uterus through a curved guide tube adapted to be inserted through the vagina and cervix of a woman in labor. The catheter tube contains a sterile liquid and is closed at both ends by a seal which is capable of transmitting pressure from the liquid within the catheter to an external liquid. In a preferred embodiment, a limp membrane is used to couple the catheter tube to a strain gauge or the like for measuring pressure. The catheter end within the uterus includes a number of pinholes and a capillary material within the tube to prevent loss of the catheter liquid. Alternatively, and particularly where it is desired not to rupture the amniotic membrane, a second limp membrane may be used as the means for coupling between the catheter liquid and the uterus.

Where the uterine end of the catheter includes a series of pinholes, the guide tube is sealed and the catheter tube is packaged with its uterine end in a sterile liquid inside the guide tube.

5 Claims, 6 Drawing Figures

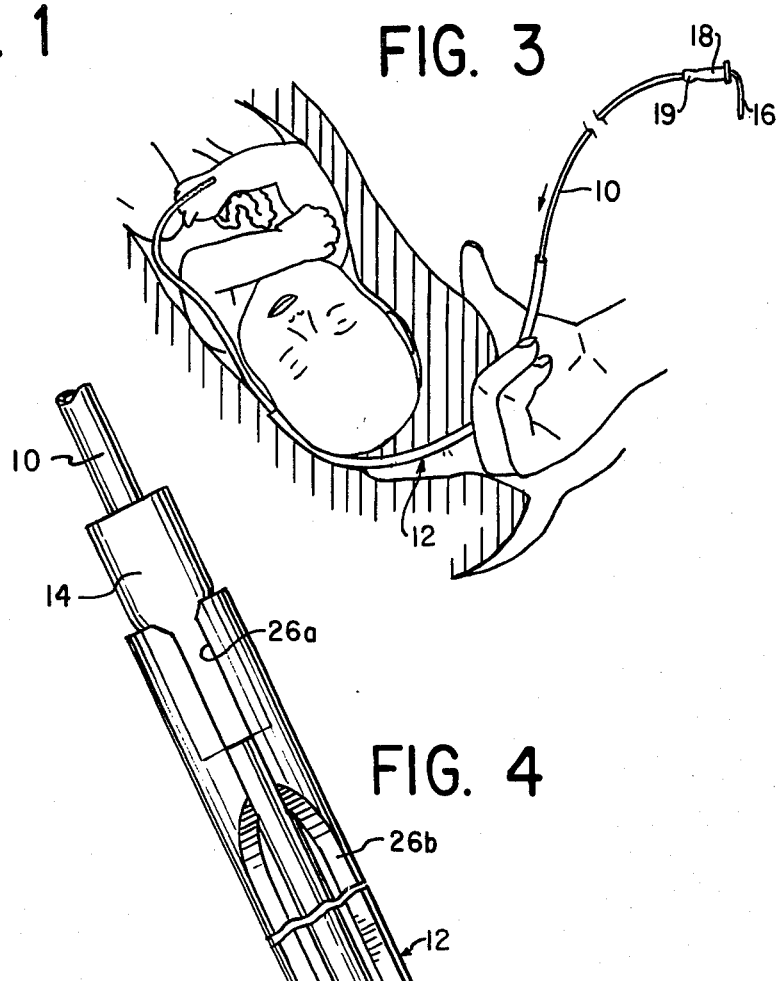
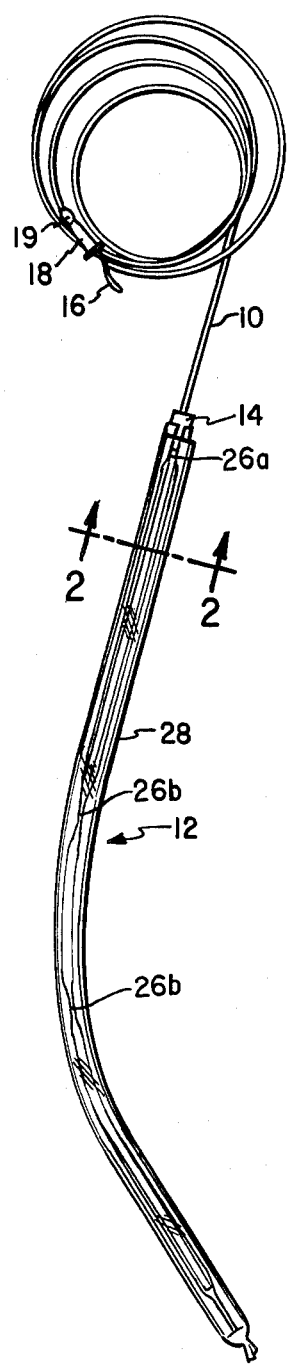
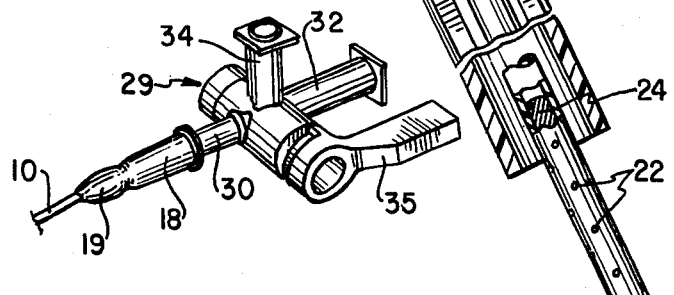
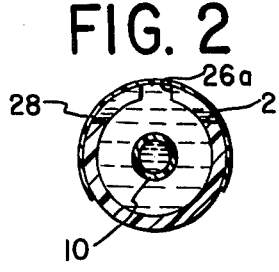
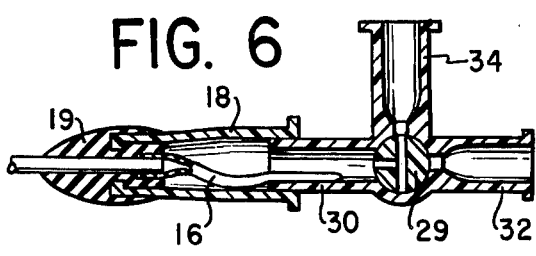

CATHETER FOR MEASURING INTRAUTERINE PRESSURE

This invention concerns the measurement of intrauterine pressure. More specifically, this invention pertains to a catheter adapted to be used for the measurement of intrauterine pressure during labor.

Fetal monitoring is a standard procedure for monitoring the condition of a fetus during childbirth. In most cases, fetal heart rate and intrauterine pressure are measured and separately plotted on a strip-chart recorder. By examining these curves, the onset of certain distress conditions can be detected so that appropriate remedial action can be taken earlier than would otherwise be possible.

To measure intrauterine pressure a catheter may be inserted into the uterus and filled with liquid so that the force of the intrauterine contractions can be transmitted through the uterine fluids and the liquid in the catheter to a pressure-measuring device such as a strain gauge or the like.

In prior art applications of intrauterine catheters of the type described, a cumbersome procedure is required to fill the catheter with liquid and then couple the catheter to the strain gauge to complete a liquid path or column from the uterus to the gauge. Conventionally, the catheter is inserted through a relatively rigid guide tube which is curved to conform to the vaginal canal. The catheter is pushed through the guide tube until the uterine end of the catheter is located correctly within the uterus. The sterile liquid is injected by means of a syringe and suitable adaptor into the catheter. It is then necessary to slide the guide tube off the catheter which requires removal of the adaptor and syringe through which the liquid was injected into the catheter.

After the guide tube has been removed, the catheter is coupled by means of the adaptor to a three-way stopcock, with the other inlets of the stopcock being connected, respectively, to the luer fitting of the strain gauge and the syringe. This enables the bleeding of air which is likely to enter the system during insertion of the catheter into the uterus. The bleeding operation requires first that water be again injected into the catheter. The catheter is then closed by the stopcock and the syringe used to inject water into the strain gauge dome until all air is removed. Next, the syringe is removed to obtain a "zero" setting by opening the strain gauge (after the air bubbles have been removed) to atmosphere. The "off" lever on the three-way stopcock is then rotated so that the catheter is coupled directly to the strain gauge.

During use, known intrauterine catheters of the type described may be "plugged" by materials within the uterus. If this happens, pressure measurements are no longer meaningful and the catheter must therefore be cleaned which invariably requires that the system be again bled as described above.

Despite the use of a sterile liquid, because the liquid injection and air bleeding procedures take place in an insterile environment, use of these standard catheters too frequently is accompanied by substantial risk of infection.

The present invention provides a catheter intended to be used for measuring intrauterine pressure which is substantially easier to use than known intrauterine catheters. More particularly, the present invention provides a catheter for intrauterine pressure measurements wherein the time-consuming and complex air-bleeding operations described above are no longer required. Moreover, the catheter of the invention is less susceptible to plugging during use, and, because no external liquid is required, the risk of infection is substantially reduced.

Briefly, in accordance with the invention, a catheter tube is filled with a sterile liquid and sealed at both the uterine and gauge ends by means which can transmit liquid pressure changes without significant energy transformation. In a preferred embodiment, a limp membrane is used to couple between the liquid pressure within the catheter and the liquid environment outside of it, either within the strain gauge or in the uterus. The catheter is inserted through a guide tube which, in configuration, is similar to standard guide tubes, but which is slit longitudinally so that the guide tube can be removed from around the catheter by pulling the catheter through the slot. This eliminates the need for pulling the entire length of the catheter through the guide tube. Because the liquid is sealed within the catheter, there is no likelihood that air will enter into the system during insertion of the catheter; as a result, the time-consuming air-bleeding operation described above is no longer required and the gauge end of the catheter may be inserted directly into the strain gauge or the standard stopcock. The risk of infection is also reduced.

The invention is described in detail below with reference to the drawings; wherein FIG. 1 is a plan view of a catheter and guide tube according to a preferred embodiment of the invention;

FIG. 2 is a sectional view along the line 2—2 of FIG. 1;

FIG. 3 is a diagrammatic illustration showing the manner in which the catheter is inserted into the uterus;

FIG. 4 is a side view, partially in section, showing details of the guide tube in the uterine end of the catheter;

FIG. 5 is a perspective view of a standard threeway stopcock to which the gauge end of the catheter according to the invention has been secured; and FIG. 6 is a side sectional view of the stopcock and gauge end of a catheter according to a preferred embodiment of the invention.

FIG. 1 shows the entire catheter device exclusive of the packaging which would maintain the device in a sterile environment during shipment. The catheter tube is shown at 10 and the guide tube at 12. The guide tube 12 is curved to conform to the vaginal canal to assist in inserting the catheter tube 10 into the uterus. Preferably, guide tube 12 is made of a moderately hard plastic material which will maintain its basic shape during use yet be capable of at least slight bending. Catheter tube 10 is substantially longer and more flexible than guide tube 12 and extends through an elastomeric plug 14 which seals the gauge end of guide tube 12 and holds the uterus end of the catheter tube 10 within the guide tube 12. Catheter tube 10, for example, may be made of polyethylene.

The catheter tube 10 is filled with a sterile liquid (e.g., distilled water) and is closed at the gauge end by a limp membrane 16 in the form of an ellipsoid sack (see FIG. 6). A conically shaped connecting member 18, for coupling to the stopcock shown in FIGS. 5 and 6, envelopes the limp membrane 16. The membrane 16 and connecting member 18 may be sealed to the gauge end of catheter tube 10 by a latex sealant 19 or in any other suitable way.

The membrane 16 is an important part of the device and, in effect, serves as a passive or "floating" membrane in the liquid column from the uterus to the strain gauge. Desirably, this passive membrane only separates the strain gauge from the catheter tube 10 and introduces no energy transformation into the system, as would occur in the case of a taut balloon, for example. This means that it must be capable of a volume expansion sufficient to reflect faithfully pressure changes associated with any uterine contraction without causing the membrane to be placed under tension. Tension in the membrane would necessarily involve some energy transformation which would affect the fidelity of the gauge measurements. In this specification, the term "limp membrane" is thus intended to mean a passive membrane which essentially neither absorbs from nor delivers energy to the liquid column over the pressure range of interest. As an example, the limp membrane 16 may be made of latex rubber.

The uterine end of the catheter tube 10 includes a series of pinholes 22 in the cylindrical surface of the tube. It is necessary that the uterine pressure be transmitted to the liquid within the catheter tube 10 and that the liquid within the tube not spill during packaging, transit or use. For this purpose, about one inch of the uterine end of catheter 10 is packed with a material 24 which functions as a multiplicity of longitudinal capillaries. One suitable material for this purpose is cotton thread wound in a spiral although numerous other materials may be used. The capillaries enable the pressure from the liquid within the uterus to be transmitted to the liquid sealed within the catheter 10 while substantially preventing the introduction of air into the catheter. In the case of the spirally coiled cotton thread, there is a delay of about one second between the uterine contraction and the time it takes to register the full force of the contraction on the gauge, which is acceptable.

The guide tube 12 includes a longitudinal slot 26 along its entire length. The slot 26 includes section 26A and 26B. The width of the slot sections 26A is less than the width of slot sections 26B and is also slightly less than the outer diameter of the tube 10. This assures that the catheter tube 10 will not accidentally be removed from the guide tube 12 during use. Although guide tube 12 is made of a relatively rigid material, it is in fact slightly flexible and after the guide tube is removed from the patient, the slot sections 26A can be forced apart a sufficient distance to permit removal of the tube 10.

For packaging purposes, and to further minimize the likelihood of introducing air into the catheter tube 10 during transit and use, the guide tube 12 may be filled with a sterile liquid, such as distilled water, and the entire device sealed by a suitable polymeric film 28. The film 28 must be watertight to seal the tube but, for reasons which are explained below, it should be also made of a material which will readily tear when it is desired to force the catheter tube 10 through the longitudinal slot 26 in guide tube 12.

The invention does not require the use of a stopcock and can be coupled directly to the dome of a strain gauge, for example. However, since standard current procedures use stopcocks, and it is contemplated that the invention will be fully compatible with existing apparatus, the preferred embodiment is described for use with a conventional stopcock 29 as illustrated in FIGS. 5 and 6.

The stopcock 29 includes three transverse fittings 30, 32 and 34 for connection to a catheter tube, strain gauge and syringe, respectively. An "off" lever 35 can be rotated to connect any two of these fittings, the direction in which lever 35 extends indicating the "off" or blocked fitting. When lever 35 points downwardly, the liquid column is open to the atmosphere so that the gauge can be properly "zeroed".

The method of using the catheter illustrated in FIGS. 1, 2 and 4 is explained with reference to the diagram of FIG. 3. The guide tube 12 with the uterine end of the catheter tube 10 sealed within it (see FIG. 1) is inserted into the vaginal canal by the doctor. When the guide tube 12 is in place, the doctor removes the plug 14 and pushes the catheter tube 10 to cause its uterine end to break the seal at the uterine end of the guide tube 12 (the bottom of FIG. 1). The catheter is then inserted until it is located approximately as indicated in FIG. 3. This is normally indicated by the position of an indicator mark (not shown) on tube 10. The doctor then holds the catheter tube 10 in place and removes the guide tube 12. When the guide tube has been removed from the patient, the catheter tube 10 is forced through the slot 26 and the guide tube is discarded. The connecting member 18 is then pushed onto the stopcock fitting 30.

The invention substantially simplifies the procedures required to measure intrauterine pressure using an intrauterine catheter. Using the catheter of the invention, it is no longer necessary to fill the catheter with liquid prior to or during catheter insertion and then undertake the individual steps required to bleed the system of air.

After the catheter is in place, the operation is essentially the same as with existing catheters. When the uterus contracts, the pressure of the liquid within the uterus is coupled through the pinholes 22 and the capillary material 24 to the liquid within the tube 10. This pressure is coupled through the limp membrane 16 (without energy transfer) to the liquid in the dome of the strain gauge and the measurement then indicated in conventional manner, by a strip-chart recorder or the like.

It is contemplated that a limp membrane, such as membrane 16 or other passive membrane, may be used at the uterine end of the catheter 10 in place of the pinholes 22 and capillary material 24. A catheter with membrane at both the gauge and uterus ends would be completely self-contained and, therefore, there would be no need to package the device within the sealed guide tube 12 as shown in FIGS. 1, 2 and 4. This embodiment of the invention could be used to take pressure readings outside of the amniotic membrane, where desired.

What is claimed is:

1. An intrauterine catheter for use in measuring intrauterine pressure, comprising:
   an elongated guide tube having a slot extending its entire length and means for sealing said slot, said guide tube being adapted to be inserted through the vagina and cervix of a woman in labor,
   an elongated flexible catheter tube within said guide tube for providing a liquid coupling from a patient's uterus to a suitable pressure measuring device, said catheter tube being filled with liquid and including a plurality of pinholes at the uterine end of the catheter tube, and a diaphragm sealing the opposite end of the catheter tube for enabling the transmission of liquid pressure changes without significant energy transformation, the outer diameter of said catheter tube being small enough to pass through the slot in said guide tube.

2. A catheter according to claim 1, wherein said diaphragm comprises a limp membrane.

3. A catheter according to claim 1, including a resilient plug sealing one end of said guide tube for retaining the catheter tube in a fixed position within said guide tube.

4. A catheter according to claim 1, including means for sealing the ends of said guide tube with the uterine end of said catheter tube within said guide tube, and a liquid within said sealed guide tube.

5. A catheter according to claim 1, including a connector enveloping said diaphragm for mechanically connecting said catheter tube to said pressure measuring device.

* * * * *